United States Patent [19]

Bushéy

[11] Patent Number: 5,254,123
[45] Date of Patent: Oct. 19, 1993

[54] COMPRESSIVE DEVICE FOR ULTRASOUND-GUIDED REPAIR OF PSEUDOANEURYSMS

[75] Inventor: Ken Bushéy, Davis, Calif.
[73] Assignee: Complete System Diagnostics, Inc., Davis, Calif.
[21] Appl. No.: 840,450
[22] Filed: Feb. 24, 1992
[51] Int. Cl.⁵ ............................................ A61B 19/00
[52] U.S. Cl. .................................................... 606/130
[58] Field of Search ................. 606/130, 201; 604/116

[56] References Cited

U.S. PATENT DOCUMENTS

| | | | |
|---|---|---|---|
| 3,779,249 | 12/1973 | Semler | 128/325 |
| 4,233,980 | 11/1980 | McRae et al. | 128/325 |
| 4,497,325 | 2/1985 | Wedel | 128/754 |
| 4,572,182 | 2/1986 | Royse | 128/325 |
| 4,638,799 | 1/1987 | Moore | 128/303 |
| 4,653,509 | 3/1957 | Oloff et al. | 606/130 |
| 4,846,173 | 7/1989 | Davidson | 606/130 |
| 4,898,178 | 2/1990 | Wedel | 128/662.05 |
| 5,004,457 | 4/1991 | Wyatt et al. | 606/130 |
| 5,047,036 | 9/1991 | Koutrouvelis | 606/130 |
| 5,116,344 | 5/1992 | Sundqvist | 606/130 |

OTHER PUBLICATIONS

Vmueller, Microsurgery; The New Frontier, Apr. 1965.

*Primary Examiner*—William E. Kamm
*Assistant Examiner*—J. P. Lacyk
*Attorney, Agent, or Firm*—John P. O'Banion

[57] ABSTRACT

A support apparatus (10) for transducer (12) of the type used in ultrasound-guided compression repair of arterial defects such as pseudoaneurysms and arteriovenous fistulas. The apparatus (10) includes a plurality of articulating arms which are releasably lockable into selected positions. Attached to one end of the arm structure is a base member (32) which supports the arm structure in a free-standing configuration. Located at the other end of the arm structure is a clamp member (16) having a central body which receives and holds the transducer (12). Pressure applied by the transducer is controlled by adjustment of a guide member (20) which is positioned between the arm structure and the clamp member (16).

11 Claims, 4 Drawing Sheets

COMPRESSIVE DEVICE FOR ULTRASOUND-GUIDED REPAIR OF PSEUDOANEURYSMS

BACKGROUND OF THE INVENTION

1. Field of the Invention

This invention relates generally to arterial compression devices, and more particularly to a device for supporting an ultrasound transducer for application of pressure during ultrasound-guided compression repair of arterial defects such as a pseudoaneurysm or arteriovenous fistula.

2. Description of the Background Art

Blind manual compression has been routinely used to close an arterial puncture after angiography or other procedures are performed in which a needle or catheter is inserted and removed from an artery. Manual compression of the area surrounding the arterial wound is applied either by hand or by a clamping device until coagulation occurs. U.S. Pat. No. 3,779,249 issued to Semler on Dec. 18, 1973, discloses a free-standing artery clamp which is used to hold a pressure pad over an arterial puncture following catheterization. U.S. Pat. No. 4,233,980 issued to McRae et al. on Nov. 18, 1980, discloses a freestanding hemostatic compression clamp and bladder which is used to apply uniformly distributed pressure over an artery to produce hemostasis. U.S. Pat. No. 4,572,182 issued to Royse on Feb. 25, 1986, discloses a pressure pad for use with a clamp such as that shown in U.S. Pat. No. 3,779,249, the pressure pad including a notched portion facilitating placement over a catheter so that pressure can be applied immediately prior to and after removal of the catheter.

In addition to the foregoing devices, other devices exist for positioning needles or ultrasound transducers. For example, U.S. Pat. No. 4,638,799 issued to Moore on Jan. 27, 1987, discloses a needle guide apparatus for discolysis procedures. U.S. Pat. No. 4,898,178 issued to Wedel on Feb. 6, 1990, discloses a monolithic disposable needle guide for ultrasound transducers. U.S. Pat. No. 4,497,325 issued to Wedel on Feb. 5, 1985, discloses an ultrasound needle, biopsy instrument or catheter guide. However, these devices are not suited for compression repair of arterial defects.

Recently, the incidence of postcatheterization femoral artery pseudoaneurysms and arteriovenous fistulas has increased as a result of the use of larger percutaneous instruments and periprocedural heparin. While standard treatment has been open surgical repair of the arterial defect, non-surgical techniques have now been developed to cause the formation of a hemostatic plug in the arterial defect by accurately applying blunt pressure until blood flow in the extraluminal track is eliminated. These new techniques require the use of an ultrasound transducer to identify the exact location of the pseudoaneurysm or fistula track. Once located, the transducer is positioned so that the pseudoaneurysm or fistula track is centered in the image, and downward force is applied with the transducer until flow through the track is eliminated. Pressure is continued for approximately 10 to 20 minutes, after which time compression is slowly released. During application of pressure, a hemostatic plug of thrombus forms to close the arterial defect and track, thus leaving the pseudoaneurysm as a simple hematoma which will resorb spontaneously.

Constant ultrasound monitoring is required to verify that application of pressure is non-threatening and does not impair arterial flow. The length of time during which compression and monitoring must be maintained makes it difficult for a technician to manually apply pressure with the transducer. While a time period of 15 to 20 minutes of pressure is typical, there are known instances where pressure had to be maintained for as long as 120 minutes. Additionally, because pressure is typically applied in a direction essentially perpendicular to the arterial defect, the patient generally is positioned so that straight, downward pressure can be applied. During this time, the technician is unable to perform other procedures or duties.

A need exists, therefore, for a device which can both maintain the position of the transducer and apply pressure to the site of the pseudoaneurysm or arteriovenous fistula while permitting the technician to have his or her hands free. The present invention fills that need.

The foregoing patents reflect the state of the art of which the applicant is aware and are tendered with the view toward discharging applicant's acknowledged duty of candor in disclosing information which may be pertinent in the examination of this application. It is respectfully stipulated, however, that none of these patents teach or render obvious, singly or when considered in combination, applicant's claimed invention.

SUMMARY OF THE INVENTION

The present invention generally comprises an articulating support apparatus for a transducer during ultrasound-guided compression repair of arterial defects such as pseudoaneurysms and arteriovenous fistulas. During this procedure, an ultrasound transducer is positioned over the site of the arterial defect and, once positioned, the transducer is used to apply pressure to the site.

In the apparatus of the present invention, the transducer is held in place by a specially designed clamp or holder having a central opening which receives and holds the transducer, and a plurality of straight and cantilever arms which are pivotally or slidably coupled for articulating movement. Pressure applied by the transducer is controlled by adjustment of a guide member which is positioned between the arm structure and the transducer holding body. The arm assembly is supported by a base member which permits the apparatus to be placed on a generally flat surface in a freestanding configuration. Alternatively, the base member or arm assembly can be attached to a rigid surface.

The apparatus is placed near the subject experiencing the arterial defect, and the arms are adjusted until the transducer is positioned over the site of the arterial defect. The apparatus is further adjusted until the desired amount of pressure is applied by the transducer. Locking mechanisms are also provided for each of the arms so as to prevent movement of the transducer once it is adjusted into position.

An object of the invention is to accurately position a transducer during ultrasound-guided compression repair of arterial defects.

Another object of the invention is to permit a medical technician, physician, or nurse to perform ultrasound-guided compression repair of arterial defects while their hands are free to perform other tasks.

Another object of the invention is to provide for continuous compression of arterial defect sites without slippage of the transducer.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
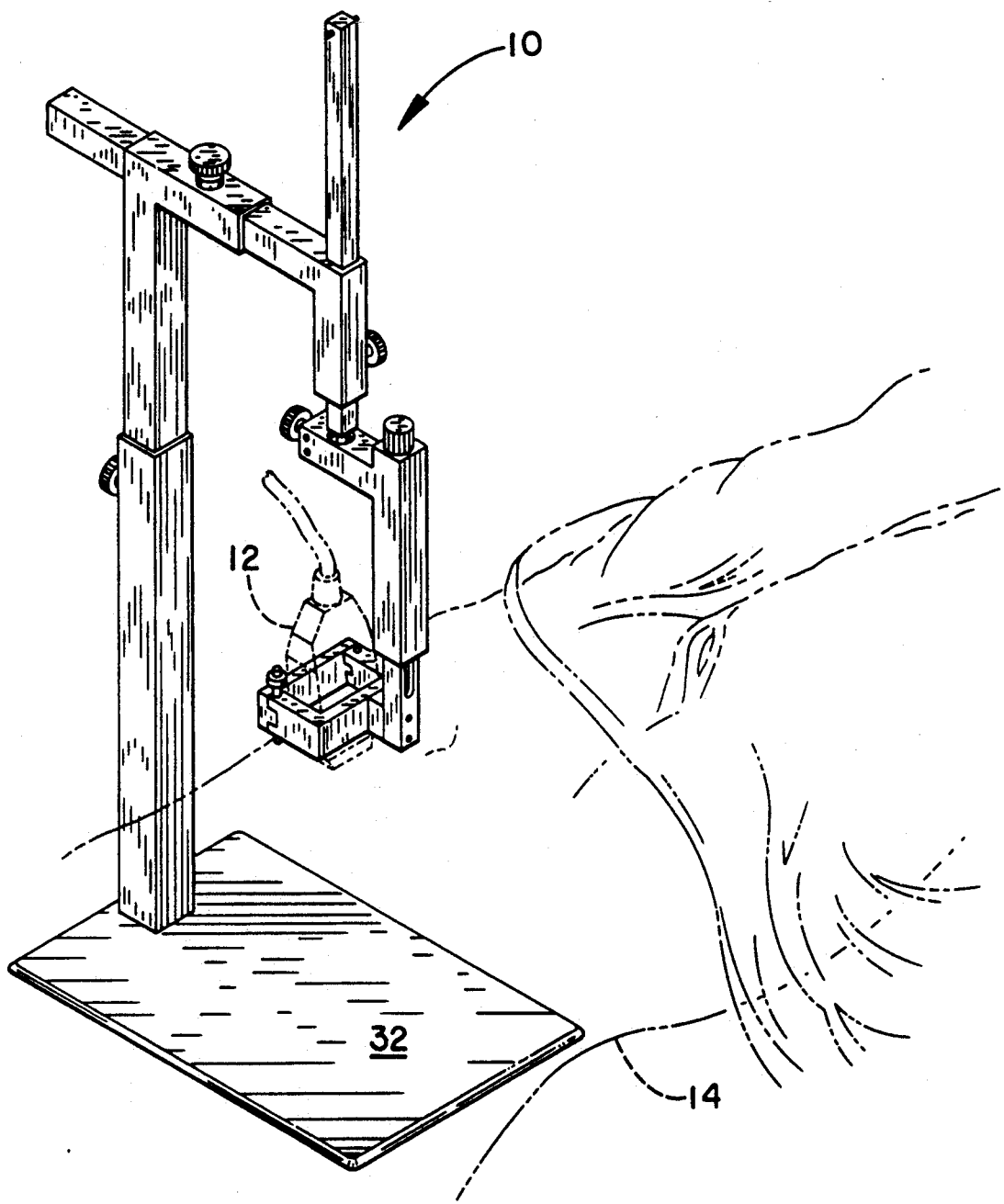
FIG. 1 is a perspective view of the apparatus of the present invention supporting a transducer shown in phantom in position over a patient shown in phantom.

Referring more specifically to the drawings, for illustrative purposes the present invention is embodied in the apparatus generally shown in the drawings identified as FIG. 1 through FIG. 4 where like references denote like parts. It will be appreciated that the apparatus may vary as to configuration and as to details of the parts without departing from the basic concepts as disclosed herein.

Figure 2:
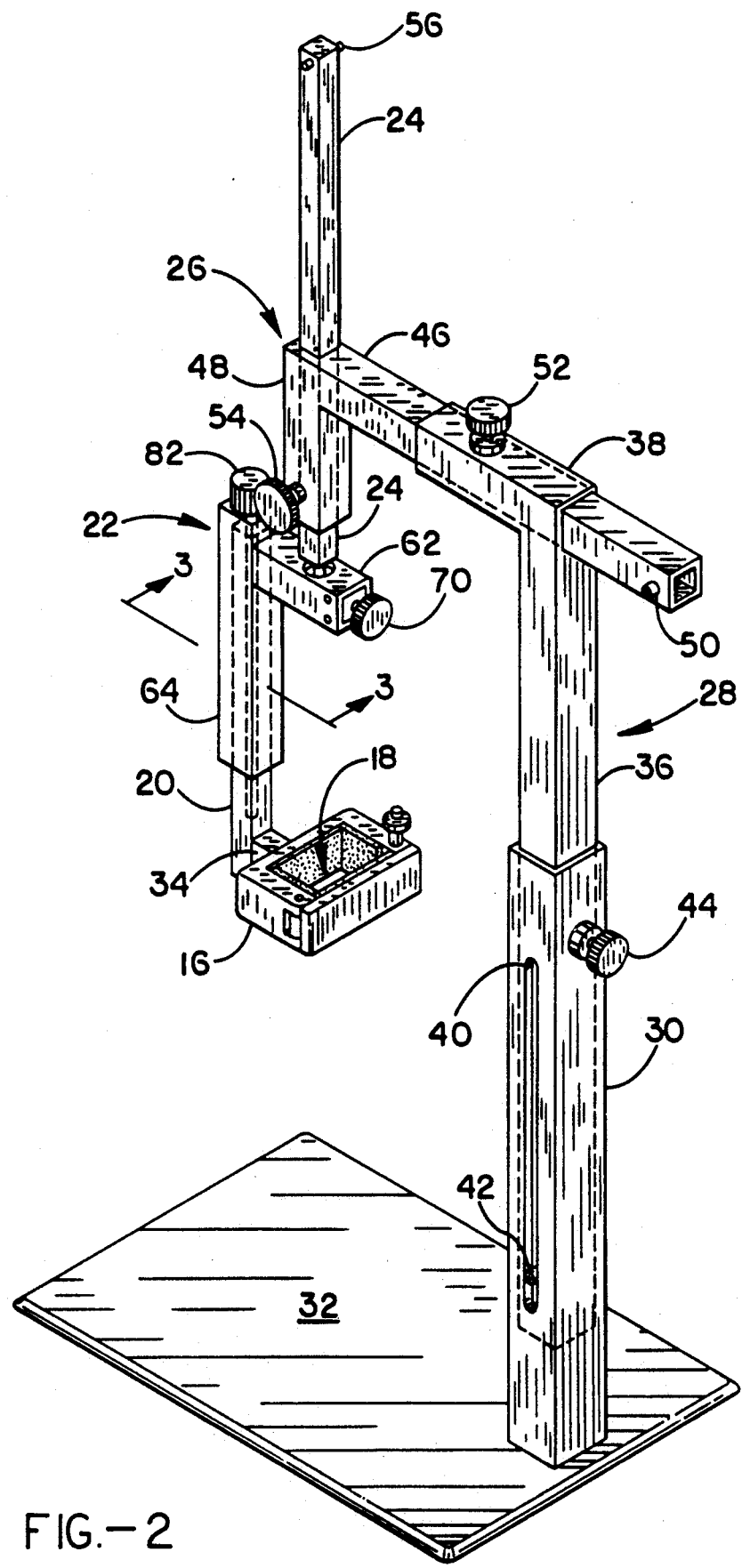
FIG. 2 is a perspective view of the apparatus of the present invention.

Referring to FIG. 1 and FIG. 2 together, the apparatus 10 of the present invention supports a transducer 12 or other similar instrument in position where compression is to be applied to patient 14. Transducer 12 is supported in position by a clamp 16, one embodiment of which is shown in detail in FIG. 3. Clamp 16 includes a receptacle 18 for holding and receiving transducer 12.

Referring now to FIG. 2, transducer clamp 16 is joined to first arm member 20 with a spacer 34 in between. First arm member 20, which is a transducer holder arm, fits within second arm member 22 and is slidably coupled thereto. Second arm member 22 is pivotally coupled to third arm member 24. Third arm member 24, which is an elongated coupling arm, fits within fourth arm member 26 and is slidably coupled thereto. Fourth arm member 26 fits within fifth arm member 28 and is slidably coupled thereto. Fifth arm member 28 fits within stand member 30 and is slidably coupled thereto. Stand member 30 is rigidly joined to base 32 which supports the entire apparatus. In this manner, once the apparatus is placed adjacent to the patient, transducer clamp 16 can be adjusted both as to vertical, horizontal, and radial position.

As can be seen, the combination of first arm member 20 and second arm member 22 effectively forms a first support means which is rotatably moveable in relation to a second support means formed by the combination of third arm member 24, fourth arm member 26, fifth arm member 28 and stand member 30. Since second arm member 22 and third arm member 24 are pivotally coupled, transducer clamp 18 can be rotated or otherwise adjusted into a sphere of positions. This is an important feature of the apparatus in that it is not always possible to position patient 14 such that the area to which pressure is to be applied by transducer 12 is vertically oriented.

In the preferred embodiment, stand member 30 is typically an elongated hollow tubular member which is rigidly joined to base 32 by welding or other common fastening techniques. Fifth arm member 28 is typically of an "L-shaped" cantilever configuration having a first leg member 36 which slides within stand member 30, and a substantially perpendicular hollow second leg member 38 for receiving fourth arm member 26. Stand member 30 includes a slot 40 in which pin 42 slides. Pin 42 is joined to first leg member 36. This configuration limits the distance of travel of fifth arm member 28 and prevents it from being inadvertently separated from stand member 30 during adjustment. Knob 44 is provided on stand member 20 to tighten a cinch pin or screw bolt against first leg member 36 to lock in position and prevent further movement of fifth arm member 28 once it is adjusted in position.

Fourth arm member 26 is typically of an "L-shaped" cantilever configuration having a third leg member 46 which slides into second leg member 38, and a substantially perpendicular hollow fourth leg member 48 for receiving third arm member 24. Third leg member 46 includes a pin 50 which prevents fourth arm member 26 from being inadvertently separated from fifth arm member 28 during adjustment. Note also that second leg member 38 includes a knob 52 which serves to tighten a cinch pin or screw bolt against third leg member 46 to lock in position and prevent further movement of fourth arm member 26 once it is adjusted in position.

Third arm member 24 slides into fourth leg member 48 and is locked into place by knob 54 which serves to tighten a cinch pin or screw bolt against third arm member 24. Third arm member 24 also includes a pin 56 at one end which prevents separation of third arm member 24 from fourth arm member 26 during adjustment.

Figure 3:
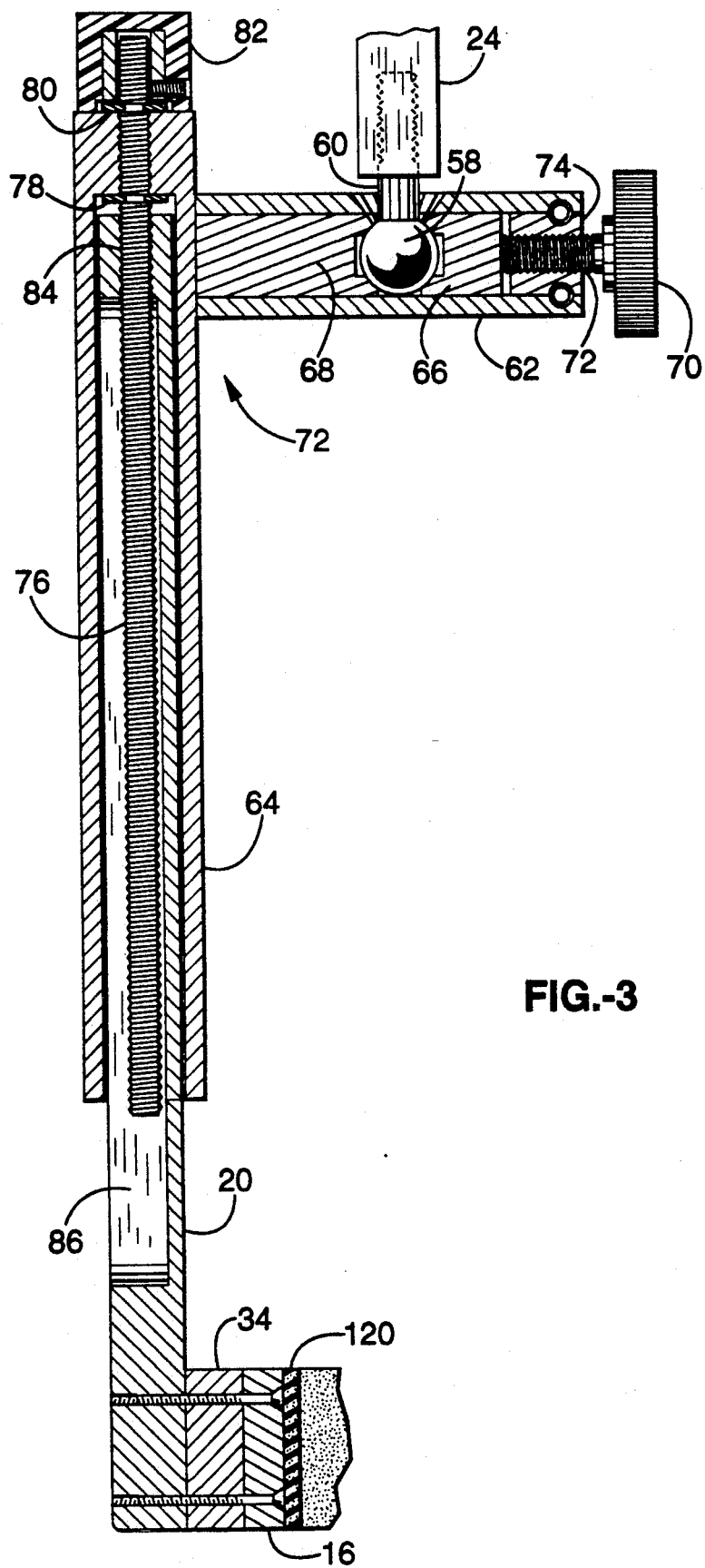
FIG. 3 is a cross-section view of the apparatus shown in FIG. 2 taken through line 3—3.

Referring also to FIG. 3, third arm member 24 includes a ball 58 joined at one end by threaded shaft 60. This permits third arm member 24 to be pivotally coupled to second arm member 22. Second arm member 22 is typically of an "L-shaped" cantilever configuration having a fifth leg member 62 which receives ball 58, and a substantially perpendicular hollow sixth leg member 64 for receiving first arm member 20.

Located within and slidably coupled to fifth leg member 62 is a piston 66, one end of which is rounded and tapered to seat against ball 58. Also located within fifth leg member 62 is a stationary seat 64 which also has an end which is rounded and tapered to seat against ball 58. When it is desired to lock second arm member 22 and third arm member 24 into position, knob 70 is rotated until threaded shaft 72 compresses piston 66 against ball 58. End plug 74 provides a threaded receptacle attached to fifth leg member 62 for receiving threaded shaft 72.

Running lengthwise through sixth leg member 64 is a threaded shaft 76. The lower end of threaded shaft 64 floats, while the upper end of threaded shaft 64 is rotatably coupled to sixth leg member 64. Threaded shaft 76 rotates freely within sixth leg member 64 and is coupled thereto with clip washers 78, 80 which hold it in place. Knob 82 is joined to the upper end of threaded shaft 76 to facilitate rotation thereof. One end of first arm member 20 includes threads 84 through which threaded shaft 76 extends. By rotating knob 82, first arm member 20 can be extended or retracted. Note also that first arm member 20 includes a slot 86 through which threaded shaft 76 is housed.

While the tubular arm and leg members of the apparatus 10 are shown to be square, it should be noted that they may also be round or other shapes without departing from the scope of the invention. In addition, any rigid material such as aluminum, steel, plastic or the like can be used in the construction of apparatus 10. Stainless steel is typically preferred in a hospital environment.

Figure 4:
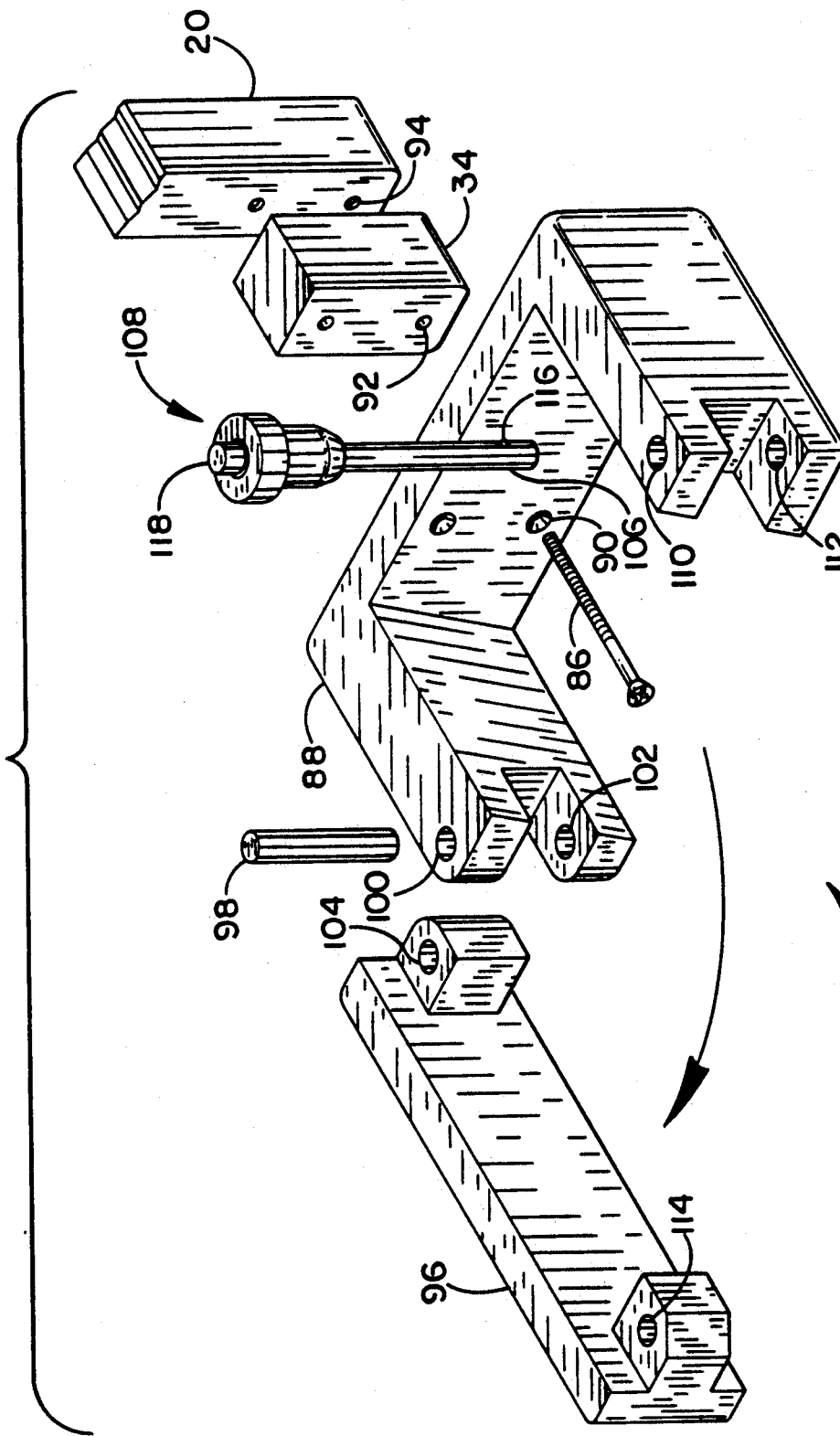
FIG. 4 is an exploded view of one embodiment of the transducer clamp assembly of the apparatus shown in FIG. 2.

Referring now to FIG. 4, transducer clamp 16 includes, as a first clamp member, a clamp body 88 which is joined to first arm member 20 using screws 86 or the like which extend through holes 90, through holes 92 and into threaded, holes 94. Coupled to clamp body 88 as a second clamp member is clamp door 96 which pivots about pin 98. Pin 98 extends through holes 100, 102 as well as through hole 104 to provide this pivot. When clamp door is closed, the shaft 106 of lock 108 is extended through holes 110, 112 as well as through hole 114. Locking ball 116 will then prevent lock 108 from being removed until button 118 is depressed. Button 118 is normally extend by means of a spring (not shown) and is attached to a shaft (not shown) which causes locking ball 116 to be in either a fixed or moveable position. The closure of clamp body 88 and clamp door 96 forms receptacle 18 into which transducer 12 can be inserted and supported. Referring also to FIG. 3, transducer clamp 16 includes seating material 120 which is foam, rubber or the like, to line the surface defining receptacle 18. This material prevents slippage of transducer 12.

It should also be noted that FIG. 4 shows one embodiment of transducer clamp 16. This particular configuration is suited for the physical characteristics of certain transducers. Other shapes and configurations of transducer clamp 16 are equally suited depending upon the particular transducer 12 to be used.

Accordingly, it will be seen that this invention provides for accurate positioning and application of pressure during ultrasound-guided compression repair of arterial defects. Although the description above contains many specificities, these should not be construed as limiting the scope of the invention but as merely providing illustrations of some of the presently preferred embodiments of this invention. Thus the scope of this invention should be determined by the appended claims and their legal equivalents.

I claim:

1. An apparatus for supporting an ultrasound transducer to apply pressure to a localized portion of a human body, comprising:
   (a) a first clamp member, said first clamp member having first and second ends;
   (b) a second clamp member, said second clamp member having first and second ends, one end of said first clamp member pivotally coupled to one end of said second clamp member, said first and second clamp members having opposing ends adapted to receive means for releasably locking said first and second clamp members in a fixed position, said first and second clamp members adapted to receive and hold an ultrasound transducer;
   (c) first support means for supporting said clamp members, said first support means coupled to said clamp members;
   (d) second support means for supporting said first support means, said second support means pivotally coupled to said first support means; and
   (e) a base, said second support means coupled to said base.

2. An apparatus for supporting an ultrasound transducer to apply pressure to a localized portion of a human body, comprising:
   (a) transducer holding means adapted for receiving and holding an ultrasound transducer;
   (b) a first arm member, said first arm member joined to said transducer holding means;
   (c) a second arm member, said second arm member slidably coupled to said first arm member;
   (d) a third arm member, said third arm member pivotally coupled to said second arm member;
   (e) a fourth arm member, said fourth arm member slidably coupled to said third arm member;
   (f) a fifth arm member, said fifth arm member slidably coupled to said fourth arm member; and
   (g) an elongated upright stand member, said stand member joined to said base, said stand member slidably coupled to said fifth arm member.

3. The apparatus recited in claim 2, further comprising:
   (a) first locking means for releasably locking the position of said second arm member relative to said first arm member; and
   (b) second locking means for releasably locking the position of said second arm member relative to said second support means.

4. The apparatus recited in claim 3, further comprising:
   (a) third locking means for releasably locking the position of said fourth arm member relative to said third arm member;
   (b) fourth locking means for releasably locking the position of said fifth arm member relative to said fourth arm member; and
   (c) fifth locking means for releasably locking the position of said stand member relative to said fifth arm member.

5. An apparatus for supporting a transducer of the type used in ultrasound-guided compression repair of pseudoaneurysms and other arterial defects, comprising:
   (a) a base;
   (b) a first clamp member and a second clamp member, each of said clamp members having first and second ends, said first and second clamp members forming a receptacle adapted for receiving a transducer, one end of said first clamp member pivotally coupled to one end of said second clamp member, the other end of said first and second clamp members adapted to receive means for releasably locking said first clamp member to said second clamp member;
   (c) first support means for supporting said clamp members, said clamp members joined to said first support means; and
   (d) second support means for supporting said first support means, said second support means pivotally coupled to said first support means, said second support means joined to said base.

6. The apparatus recited in claim 5, wherein said first support means comprises:
   (a) a first arm member, said first arm member joined to said clamping means; and
   (b) a second arm member, said second arm member slidably coupled to said first arm member, said second arm member pivotally coupled to said second support means.

7. The apparatus recited in claim 6, further comprising:
  (a) first locking means for releasably locking the position of said second arm member relative to said first arm member; and
  (b) second locking means for releasably locking the position of said second arm member relative to said second support means.

8. The apparatus as recited in claim 5, wherein said second support means comprises:
  (a) a first arm member, said first arm member pivotally coupled to said first support means;
  (b) a second arm member, said second arm member slidably coupled to said first arm member;
  (c) a third arm member, said third arm member slidably coupled to said second arm member; and
  (d) an upright stand member, said stand member joined to said base, said stand member slidably coupled to said third arm member.

9. The apparatus recited in claim 8, further comprising:
  (a) first locking means for releasably locking the position of said first arm member relative to said second arm member;
  (b) second locking means for releasably locking the position of said second arm member relative to said third arm member;
  (c) third locking means for releasably locking the position of said third arm member relative to said stand member; and
  (d) fourth locking means for releasably locking the position of said first arm member relative to said first support means.

10. An apparatus for supporting an ultrasound transducer during ultrasound-guided compression repair of arterial defects, comprising:
  (a) a base;
  (b) an elongated upright first tubular member, said first tubular member joined to said base;
  (c) a first cantilever arm, said first cantilever arm including a first leg member and a tubular second leg member, said first leg member joined to said second leg member, said first leg member positioned substantially perpendicular to said second leg member, said first leg member slidably received within said first tubular member;
  (d) a second cantilever arm, said second cantilever arm including a third leg member and a tubular fourth leg member, said third leg member joined to said fourth leg member, said third leg member positioned substantially perpendicular to said fourth leg member, said third leg member slidably received within said second leg member of said first cantilever arm, said fourth leg member positioned substantially parallel to said first tubular member, said fourth leg member extending toward said base;
  (e) an elongated coupling arm, said coupling arm slidably received within said fourth leg member;
  (f) a third cantilever arm, said third cantilever arm including a fifth leg member and a tubular sixth leg member, said fifth leg member joined to said sixth leg member, said fifth leg member positioned substantially perpendicular to said sixth leg member, said fifth leg member pivotally coupled to said coupling arm;
  (g) a transducer holder arm, said transducer holder arm slidably received within said sixth leg member; and
  (h) a transducer holder, said transducer holder joined to said transducer holder arm.

11. The apparatus recited in claim 10, further comprising:
  (a) first locking means for releasably locking the position of said first cantilever arm relative to said first tubular member;
  (b) second locking means for releasably locking the position of said second cantilever arm relative to said first cantilever arm;
  (c) third locking means for releasably locking the position of said second tubular member relative to said second cantilever arm;
  (d) fourth locking means for releasably locking the position of said third cantilever arm relative to said coupling arm member; and
  (e) fifth locking means for releasably locking the position of said transducer holder arm relative to said third cantilever arm.

* * * * *